United States Patent [19]

Bergersen

[11] Patent Number: 4,856,992

[45] Date of Patent: Aug. 15, 1989

[54] PREFORMED BANDS WITH LINGUAL EXTENSIONS

[76] Inventor: Earl O. Bergersen, 950 Green Bay Rd., Winnetka, Ill. 60093

[21] Appl. No.: 116,671

[22] Filed: Nov. 4, 1987

[51] Int. Cl.⁴ .............................................. A61C 3/00
[52] U.S. Cl. ......................................... 433/18; 433/7; 433/23
[58] Field of Search ..................... 433/17, 18, 19, 20, 433/21, 22, 23, 24, 7

[56] References Cited

U.S. PATENT DOCUMENTS 3,162,948 12/1964 Gerber .................................... 433/23
4,573,914 3/1986 Nord ...................................... 433/18

Primary Examiner—Noah P. Kamen
Attorney, Agent, or Firm—Hill, Van Santen, Steadman & Simpson

[57] ABSTRACT

A preformed molar band is provided for use in human dentition correction which includes a wire extension preformed to lie against the lingual surface of the posterior teeth including the canine which has a more easily bendable portion anterior to the canine to permit the wire to be bent in the mouth to wrap around the mesial surface of the canine.

15 Claims, 1 Drawing Sheet

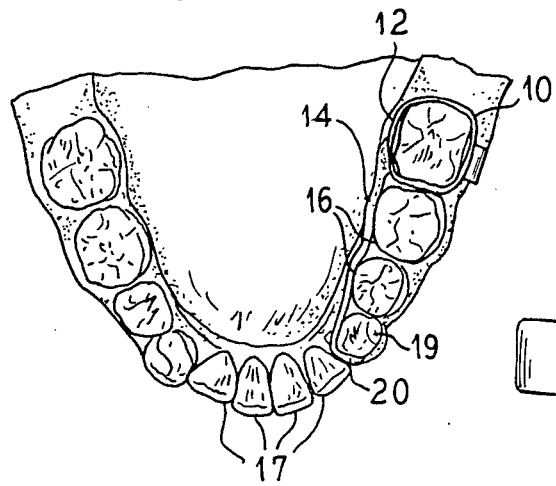
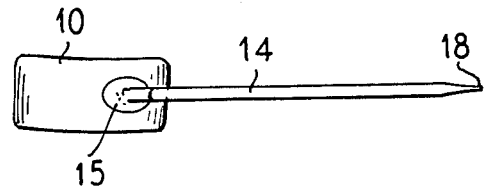
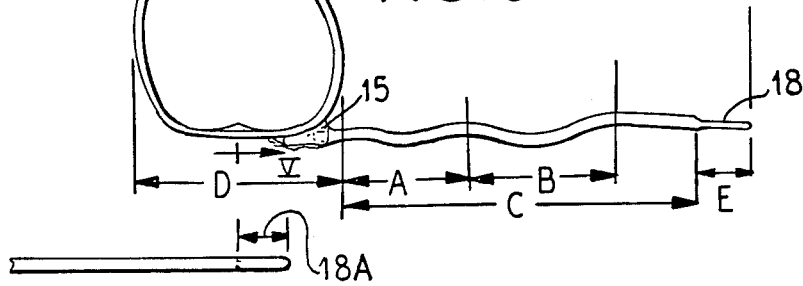
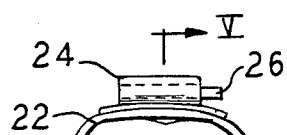
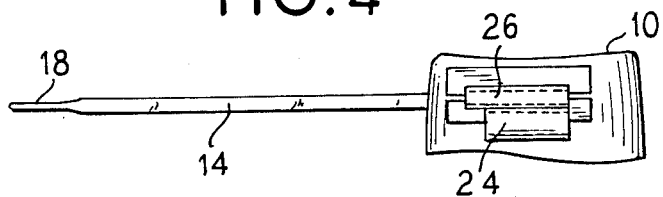
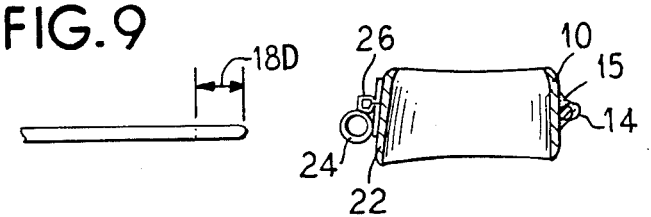

PREFORMED BANDS WITH LINGUAL EXTENSIONS

BACKGROUND OF THE INVENTION

1. Field of the Invention

The present invention relates to preformed molar bands and more particularly to preformed molar bands that have a lingual wire attached to the band.

2. Description of the Prior Art

Preformed molar bands have been used along with extension wires which attach to one or more teeth anterior or posterior of the molar encircled by the band. The formation of the extension wire required a model of the patient's teeth, generally obtained by a plaster cast, and required custom bending and soldering of the wires. The extensions of the bands were glued to the teeth by glueing on the molar bands to the teeth.

The drawbacks with such arrangements included the high cost of such a procedure due to the preparation of a model and the custom bending and soldering of the wires and band and requiring usually two appointments separated by time for the laboratory work.

SUMMARY OF THE INVENTION

The present invention provides a preformed molar band for the first or second permanent molar or second deciduous molar with a preformed lingual wire presoldered onto the lingual surface of the band contoured to fit into the lingual surface of the posterior teeth anterior or posterior to the band and can bicuspids or deciduous molar or molars and can include the deciduous or permanent canines. The portion of the wire anterior to the canine is to be reduced to about one-half the diameter of the remainder of the wire, that is from about 0.030 inches to about 0.020 inches, so that it can be bent in the mouth to wrap around the mesial surface of the canine or other tooth anterior to the molar having the molar band. Therefore, as distal movement (and expansion) occurs and the molar, the space that will open up between teeth, opens mesial to the canine and gives the added space required to the incisal segment where it is needed the most.

By providing a preformed band along with a preformed lingual wire which is presoldered to the band, the amount of time required for application of the band to the patient's teeth can be significantly reduced. By providing the thinner or softer end portion of the wire, the custom bending can occur at the time of application in the mouth in a very expedient manner.

BRIEF DESCRIPTION OF THE DRAWINGS

FIG. 1 is an occlusal view of a preformed band with lingual wire extension embodying the principles of the present invention shown in place on teeth in the lower arch.

FIG. 2 is a lingual side elevational view of the preformed band of FIG. 1.

FIG. 3 is an occlusal view of the preformed band and extension alone.

FIG. 4 is a buccal side elevational view.

FIG. 5 is a sectional view taken generally along the line V—V of FIG. 3.

FIG. 6 is a side elevational view of an end of the wire which has been heat treated.

FIG. 7 is a side elevational view of an end of the wire having a plastic extension.

FIG. 8 is a side elevational view of an end of the wire which has been flatened.

FIG. 9 is a side elevational view of an end of the wire which is formed of a softer metallic material.

DESCRIPTION OF THE PREFERRED EMBODIMENT

In FIG. 1 there is illustrated a preformed molar band 10 for correcting human dentition which is illustrated as being placed around the first permanent molar 12 in the lower arch 13. The band can also be utilized on first permanent molars in the upper arch as well as second permanent molars in either the upper or lower arches and second deciduous molars in the upper or lower arches. A preformed lingual wire 14 extends from or is securely attached to the molar band 10 such as by soldering 15, the wire being preformed to fit against a lingual surface 16 of the posterior teeth, that is the teeth posterior of the incisors 17.

The wire 14 may have a diameter of about 0.030 inches (0.75 mm) or may be of varying sizes and, at a free anterior end 18, the diameter of the wire is reduced to make the end 18 more easily bendable. This is the portion of the wire that is anterior to the canine 19. The wire may be formed of stainless steel or other metals and is sufficiently hard or rigid so as to retain its shape. Because of the reduction in the diameter, the end portion of the wire is "softer" in that it can be more easily bent in the mouth to wrap around a mesial surface 20 or engage the lingual surface of the canine 19 or other tooth anterior to the molar 12. As the molar 12 moves posteriorly, the space that is opened up between the teeth will open mesial to the canine (or other engaged tooth) to give added space to the incisal segment where it generally is needed the most.

Other means for providing a "bendable" end may be provided, such as over heating the metal at an end portion 18A (FIG. 6) to "deaden" the resiliency of the wire, coating the wire with a plastic material to form a plastic extension 18B (FIG. 7) at the anterior end which may be bent at a temperature above mouth temperature to form a tooth engaging latch, flattening the wire at an end portion 18C in a vertical orientation (FIG. 8), or by forming the wire of different materials along its length to provide a "softer" wire 18D (FIG. 9) at the anterior end. The plastic extension or coating 18B may comprise a thermoset material such as polypropylene or polyvinyl chloride or a thermoplastic material such as nylon or acrylic. By any of these arrangements, the retaining means is integrated with the extension wire.

A buccal side 22 of the band 10 has a pair of buccal tubes 24, 26 attached thereto, also by soldering or welding, to receive wires for connecting the band to bands placed on other teeth as is known in the art.

In order to provide the preformed band 10 with a preformed wire 14 conforming to the lingual surface of the teeth, the following measurements are provided as an example of a band 10 applied to a first molar and can be utilized in preparing the preformed wire 14, wherein dimension A is the distance from the anterior or mesial surface of the band to a position on the wire in line with a mesial surface of the second premolars, dimension B is the distance between a mesial surface of the second premolars and a mesial surface of the first molars, C is the distance from the mesial surface of the band to the reduced portion of the wire representing the mesial surface of the canine, D is the diameter of the band and E is the length of the reduced wire portion which is to be bent against the mesial surface of the canine. Different lengths can be utilized as needed for variations in the dentitions of particular patients. All dimensions are in millimeters.

| LOWER BAND EXTENSIONS | | | | | |
|---|---|---|---|---|---|
| Band Size Circumference | Band Diameter D | A | B | C | E |
| 30 | 9.2 | 8.49 | 6.89 | 19.0 | 5.0 |
| 31 | 9.5 | 8.68 | 7.01 | 19.6 | 5.0 |
| 32 | 9.8 | 8.86 | 7.13 | 20.1 | 5.0 |
| 33 | 10.1 | 9.05 | 7.25 | 20.6 | 5.0 |
| 34 | 10.4 | 9.24 | 7.37 | 21.1 | 5.0 |
| 35 | 10.7 | 9.42 | 7.49 | 21.6 | 5.0 |
| 36 | 11.1 | 9.61 | 7.61 | 22.1 | 5.0 |
| 37 | 11.4 | 9.79 | 7.74 | 22.7 | 5.0 |
| 38 | 11.7 | 9.98 | 7.86 | 23.2 | 6.0 |
| 39 | 12.0 | 10.16 | 7.98 | 23.7 | 6.0 |
| 40 | 12.3 | 10.35 | 8.1 | 24.2 | 6.0 |
| 41 | 12.6 | 10.54 | 8.22 | 24.7 | 6.0 |
| 42 | 12.9 | 10.72 | 8.34 | 25.3 | 6.0 |

With the use of such a preformed band and preformed wire extensions with the soft, bendable or reduced diameter free end of the wire, the band and wires can be readily placed in the patient's mouth and applied to the teeth with the bending of the end of the wire 14 being the only customized step, therefore resulting in greatly reduced time and effort needed for the application of the bands.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A preformed band for use in human dentition correction to be applied to a molar tooth and having an extension wire extending from a lingual surface of said band, a retaining means formed at an anterior end of said wire and adapted to be manually deformable into engagement with a tooth positioned anterior to said molar tooth said retaining means comprising an anterior portion of said wire which is more easily bendable than a posterior portion of said wire.

2. A preformed band according to claim 1, wherein said retaining means comprises a coating on said extension wire and extending anteriorly outwardly thereof to form a tooth engaging latch to fasten the preformed band in assembly with the teeth of the user.

3. A preformed band according to claim 2 wherein said retaining means comprises a thermoset material selected from the class including polypropylene and polyvinyl chloride.

4. A preformed band according to claim 2, wherein said retaining means comprises a thermoplastic material selected from the class including nylon and acrylic.

5. A preformed band according to claim 1, wherein said retaining means is integrated with said extension wire and comprises a tooth engaging connector for attachment to an adjoining tooth thereby to lock the band and the tooth to which it is connected to an anteriorly disposed tooth in the mouth of the user.

6. A preformed band according to claim 1, wherein said retaining means comprises a reduced cross-sectional diameter portion at said anterior portion of said wire to permit said portion to be bendable around a mesial surface of said anterior tooth.

7. A preformed band according to claim 1, wherein said retaining means comprises said anterior portion of said wire being formed of a softer material than said posterior portion, said anterior portion being more easily bendable than said posterior portion.

8. A preformed band according to claim 1, wherein said retaining means comprises said anterior portion of said wire being heat treated to make said anterior portion more easily bendable than said posterior portion of said wire.

9. A preformed band according to claim 1, wherein said retaining means comprises said anterior portion of said wire being flattened in a vertical orientation to permit said anterior end to be more easily bendable in a horizontal direction than said posterior portion of said wire.

10. A preformed band according to claim 1, wherein said band is preformed with a predetermined diameter size and extension wire length to be applied to a first permanent molar.

11. A preformed band according to claim 1, wherein said band is preformed with a predetermined diameter size and extension wire length to be applied to a second permanent molar.

12. A preformed band according to claim 1, wherein said band is preformed with a predetermined diameter size and extension wire length to be applied to a second deciduous molar.

13. A preformed band according to claim 1, wherein said wire is soldered to the lingual surface of said band.

14. A preformed band according to claim 1, wherein said wire is preformed with said extension wire extending from a lingual side of said band to fit against a lingual surface of teeth anterior of said band including said anterior tooth.

15. A preformed band for use in the human dentition correction to be applied to a molar and having a lingual extension wire extending from a lingual surface of said band and preformed to fit against a lingual surface of teeth anterior to said band, said extension wire extending anterior to an anterior tooth with an anterior end portion of said wire being more easily bendable than a posterior portion of said wire to wrap around a mesial surface of said anterior tooth.

* * * * *